United States Patent [19]

Bade

[11] Patent Number: 4,497,825
[45] Date of Patent: Feb. 5, 1985

[54] PROCESS FOR THE PREPARATION OF BETAINES

[75] Inventor: Volkbert Bade, Essen, Fed. Rep. of Germany

[73] Assignee: Th. Goldschmidt AG, Essen, Fed. Rep. of Germany

[21] Appl. No.: 442,847

[22] Filed: Nov. 16, 1982

Related U.S. Application Data

[63] Continuation of Ser. No. 158,462, Jun. 11, 1980, abandoned.

[30] Foreign Application Priority Data

Jun. 30, 1979 [DE] Fed. Rep. of Germany ....... 2926479

[51] Int. Cl.$^3$ .................. C11D 3/26; A61K 31/205; A61K 7/08
[52] U.S. Cl. ............... 514/556; 260/501.13; 260/404.5; 252/544; 252/546; 252/DIG. 5; 252/DIG. 7
[58] Field of Search ............ 260/501.13, 404.5; 252/544, 546, DIG. 5, DIG. 7; 424/319, 316

[56] References Cited

U.S. PATENT DOCUMENTS

| | | | |
|---|---|---|---|
| 3,366,671 | 1/1968 | Cowen et al. | 260/501.13 |
| 3,819,539 | 6/1974 | Bloch et al. | 260/501.13 |
| 4,137,191 | 1/1979 | Lohr | 260/501.13 |
| 4,148,762 | 4/1979 | Koch et al. | 252/544 |

*Primary Examiner*—Glennon H. Hollrah
*Assistant Examiner*—Raymond K. Covington
*Attorney, Agent, or Firm*—Toren, McGeady and Stanger

[57] ABSTRACT

A method for the preparation of betaines is disclosed, the betaines having the general formula $$R^1CONH(CH_2)_xN^{\oplus}R^2R^3(CH_2)_yCOO^{\ominus}$$

in which
$R^1$ is the alkyl residue of a fatty acid with 6 to 18 carbon atoms,
$R^2$ and $R^3$ are the same or different and represent alkyl residues with 1 to 4 carbon atoms,
$x=2$ or 3, and
$y=1$, 2 or 3.

The betaines are prepared by quaternizing fatty acid amides having the formula $$R^1CONH(CH_2)_xNR^2R^3$$

with ω-halogenalkylcarboxylic acids having the formula $$X(CH_2)_yCOOH$$

wherein X is a halogen residue, and carrying out the quaternization at a pH of 7.5 to 10.5 measured at 98° C. The reaction product obtained from the process is essentially free of unreacted amides and organically linked chlorine and thus avoids the skin irritations normally associated with compounds in which such betaines are used.

10 Claims, No Drawings

PROCESS FOR THE PREPARATION OF BETAINES

This is a continuation of application Ser. No. 158,462 filed June 11, 1980, now abandoned.

BACKGROUND OF THE INVENTION

1. Field of the Invention

The invention relates to a process for the preparation of betaines.

2. Description of the Prior Art

German Auslegeschrift No. 10 62 392 describes germicidal shampoos which are obtained by reacting a fatty acid with a dialkylaminoalkylamine to form an acid amide, which is then quaternized with a halogencarboxylic acid. The betaines obtained by this reaction are surface active and may be used as detergents. They are employed especially in cosmetics, for example, as shampoos and have excellent detersive and foaming capabilities together with a germicidal effect.

More particularly, such betaines have the formula

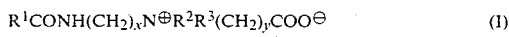

$$R^1CONH(CH_2)_xN^{\oplus}R^2R^3(CH_2)_yCOO^{\ominus} \quad (I)$$

in which $R^1$ is the alkyl residue of a fatty acid with 6 to 18 carbon atoms, $R^2$ and $R^3$ are the same or different and represent alkyl residues with 1 to 4 carbon atoms, x is 2 or 3, and y is 1, 2 or 3.

Betaines having formula I are prepared by quaternizing the fatty acid amide of the formula

$$R^1CONH(CH_2)_xNR^2R^3 \quad (II)$$

with ω-halogenalkylcarboxylic acids of the formula

$$X(CH_2)_2COOH \quad (III)$$

in which X is a halogen residue or salts of such acids.

In German Pat. No. 11 72 802, a bath salt is described which is characterized by the fact that it contains selected betaines. If this bath salt is added to bath water and the jet of water running into the bath is directed onto this bath salt, a dense, cream-like foam is formed which is stable even in the presence of soap.

These betaines are used on a large scale for the aforementioned purposes. At the same time, it turns out occasionally that persons with a very sensitive skin develop skin irritations which are evidently caused by impurities unavoidably contained in the betaines as a result of the manufacturing process.

Extensive investigations have led to the conclusion that the residue of fatty acid amide dialkylamine which has not been quaternized and the organically linked chlorine are responsible for the skin irritations. Commercially available betaines of the aforementioned formula contain from about 0.3 to 3 weight percent of free fatty acid amides.

As is well known, the quaternization reaction with halogencarboxylic acid is not quantitative but proceeds up to about 90% of the theoretical conversion, even with an excess of halogencarboxylic acid.

Many attempts to remove the unquaternized product from the reaction mixture or to convert it into a compound which does not irritate the skin have been made. For example, a process is described in German Offenlegungsschrift No. 20 63 422 which converts unreacted fatty acid amide dialkylamine into the corresponding amine oxide by the addition of hydrogen peroxide. A mixture is then obtained which consists of amine oxides as well as the desired betaine. Because of the use of larger amounts of perhydrol required, this procedure is expensive and requires an additional processing step. A further disadvantage of the conversion of the amineamides into the amineoxide amides lies in the fact that the reaction also does not proceed quantitatively. In addition, it is necessary to make certain that any excess peroxide is destroyed in order to prevent peroxide-induced skin irritations.

SUMMARY OF THE INVENTION

I have discovered a method for preparing a betaine having the structure of formula I which does not cause any skin irritation and is free of unreacted fatty acid amide dialkylamines and organically linked chlorine originating from unreacted halogenalkylcarboxylic acid.

More particularly, the method of the present invention comprises quaternizing the fatty acid amide of formula

$$R^1CONH(CH_2)_xNR^2R^3 \quad (II)$$

with ω-halogenalkylcarboxylic acids of the formula

$$X(CH_2)_2COOH \quad (III)$$

in which X is a halogen residue or salts of said acids, and wherein the quaternizing reaction is carried out in an alkaline solution which has a pH of 7.5 to 10.5 at 98° C.

DESCRIPTION OF THE PREFERRED EMBODIMENT

It is an essential feature of the reaction that the pH during the entire course of the reaction and especially also towards the end of the reaction, must have a value of 7.5 to 10.5, measured at 98° C. In the usual processes known henceforore, the reaction is carried out essentially at a neutral pH. Accordingly, German Offenlegungsschrift No. 20 63 422 indicates that the ideal reaction conditions are a low reaction temperature and a neutral pH. Under these conditions, however, the degree of conversion cannot exceed 90%. Admittedly, it is also already known that the reaction can initially be commenced in an alkaline region. However, during the course of the reaction, the pH decreases to or falls below the neutral point.

The temperature at which the pH of the reaction medium is measured is very significant since the pH in the reaction system is temperature dependent. A temperature of 98° C. which corresponds to the usual reaction temperature, has therefore been selected for determining the pH range required.

If a reaction is carried out in the pH range of 7.5 to 10.5, the presence of fatty acid amide dialkylamine cannot be detected by thin-layer chromatography after a reaction time of about 3 hours. The limit of detection by this method is 0.02 weight percent.

The pH range of 8 to 10 is especially preferred because from a pH of about 8 upwards, the excess of unreacted alkali salt of the ω-halogenalkylcarboxylic acid is decomposed. In order to make certain that no organically bound chlorine is still present in the reaction product, it is recommended that a reaction time of 8 to 10 hours be employed.

If the reaction is carried out at a pH above 10.5, there is clear decomposition of the product with phase separation. By carrying out the reaction at a pH below 7.5, the rate of the reaction is increasingly retarded, while at the same time the degree of conversion is reduced. The degree of conversion which is aimed for can no longer be attained in this pH range by means of any effort which is economically justifiable.

The advantage of the process of the present invention lies in the fact that, in contrast to the purification processes of the state of the art, for example, that disclosed in German Offenlegungsschrift No. 20 63 422, it is not the aim to convert unreacted fatty acid amide dialkylamine into a compound which does not irritate the skin. Rather, the purpose is to have the reaction proceed quantitatively without the formation of product impurities. Thus, the reaction product obtained with the present process consists practically only of the desired active ingredient and not a mixture of the desired active ingredient and unreacted impurities.

The betaine obtained according to the inventive process, after the pH has been adjusted to the desired range, may be manufactured in the usual manner. The term "manufactured" is understood to mean the adjustment of the concentration to the desired range and the optional addition of dyes, perfuming agents, other skin care products and/or thickeners.

The following examples illustrate the present invention:

EXAMPLE 1

As the fatty acid, a coconut fatty acid mixture ($C_8$ to $C_{18}$) is used. To a 3-neck flask, equipped with stirrer and reflux condenser, there are added 295 g of the N-propyl-N,N-dimethylamine amide of the fatty acid mixture and 128 g of sodium monochloroacetate, together with 775 g of water. The reaction mixture is heated slowly to 98° C. The pH is maintained at a value of 9 by the continuous addition of a 50 weight percent aqueous solution of sodium hydroxide. The course of the reaction is followed by determining the residual content of the N-propyl-N,N-dimethylamine amide of the fatty acid mixture by means of thin-layer chromatography.

After the reaction time of about 3 hours, during which about 0.1 mole of sodium hydroxide is consumed, the N-propyl-N,N-dimethylamine amide of the fatty acid mixture can no longer be detected by thin-layer chromatography. After about 8 to 10 hours, organically bound chlorine can also no longer be detected.

EXAMPLE 2

As in Example 1, a betaine is prepared from 284 g of N-laurylamidopropyl-N,N-dimethylamine, 128 g of sodium monochloroacetate and 876 g of water. The pH is kept at 7.5 during the whole reaction by the continuous addition of 50 weight percent of aqueous sodium hydroxide. After about 5 hours of reaction time, N-laurylamidopropyl-N,N-dimethylamine can no longer be detected by thin-layer chromatography.

EXAMPLE 3

As in Example 1, a betaine is prepared from 368.5 g of N-stearylamidopropyl-N,N-dimethylamine, 128 g of sodium monochloroacetate and 4468 g of water. The pH is kept at 10 during the whole reaction by the continuous addition of 50 weight percent of aqueous sodium hydroxide. After about 2 hours of reaction time, N-stearylamidopropyl-N,N-dimethylamine can no longer be detected by thin-layer chromatography. Organically bound chlorine can no longer be detected after 7 hours of reaction time.

What is claimed is:

1. A process for the preparation of betaines having the formula $$R^1CONH(CH_2)_xN^{\oplus}R^2R^3(CH_2)_yCOO^{\ominus}$$

in which
R$^1$ is the alkyl residue of a fatty acid with 6 to 18 carbon atoms,
R$^2$ and R$^3$ are the same or different and represent alkyl residues with 1 to 4 carbon atoms,
x=2 or 3, and
y=1, 2, or 3,
comprising quaternizing fatty acid amides having the formula $$R^1CONH(CH_2)_xNR^2R^3$$

with ω-halogenalkylcarboxylic acids having the formula $$X(CH_2)_yCOOH$$

in which X is a halogen residue or salts of said acids in aqueous solution wherein the entire course of the quaternizing reaction is carried out in an alkaline solution having a pH of from 7.5 to 10.5 measured at 98° C.

2. The process of claim 1 wherein the pH is from about 8 to 10.

3. The process of claim 1 wherein the quaternizing reaction is carried out for at least about 3 hours.

4. The process of claim 1 wherein the quaternization reaction is carried out for a period of from about 8 to 10 hours.

5. Betaines having the formula $$R^1CONH(CH_2)_xN^{\oplus}R^2R^3(CH_2)_yCOO^{\ominus}$$

in which
R$^1$ is the alkyl residue of a fatty acid with 6 to 18 carbon atoms,
R$^2$ and R$^3$ are the same or different and represent alkyl residues with 1 to 4 carbon atoms,
x=2 or 3, and
y=1, 2 or 3,
produced by the process of claim 1, said betaine being substantially free from fatty acid amide dialkylamine.

6. Betaines having the formula $$R^1CONH(CH_2)_xN^{\oplus}R^2R^3(CH_2)_yCOO^{\ominus}$$

in which
R$^1$ is the alkyl residue of a fatty acid with 6 to 18 carbon atoms,
R$^2$ and R$^3$ are the same or different and represent alkyl residues with 1 to 4 carbon atoms,
x=2 or 3, and
y=1, 2, or 3,
produced by the process of claim 1, said betaine being substantially free from fatty acid amide dialkylamine and substantially free from organically bound halogen.

7. A cosmetic composition containing a detersive and foaming effective amount of the betaine of claim 5 and a cosmetically acceptable carrier therefor.

8. A cosmetic composition containing a detersive and foaming effective amount of the betaine of claim 6 and a cosmetically acceptable carrier therefor.

9. The process of claim 1 wherein the pH is from about 8 to 10 and the quaternizing reaction is carried out for at least about 3 hours.

10. The process of claim 1 wherein the pH is from about 8 to 10 and the quaternizing reaction is carried out for a period of from about 8 to 10 hours.

* * * * *